(12) United States Patent
Xiao et al.

(10) Patent No.: US 11,963,894 B2
(45) Date of Patent: Apr. 23, 2024

(54) LUMEN STENT AND IMPLANT

(71) Applicant: Shenzhen Lifetech Endovascular Medical Co., Ltd., Shenzhen (CN)

(72) Inventors: Benhao Xiao, Shenzhen (CN); Chunwei Tang, Shenzhen (CN); Qin Wang, Shenzhen (CN)

(73) Assignee: LIFETECH SCIENTIFIC (SHENZHEN) CO., LTD., Shenzhen (CN)

( * ) Notice: Subject to any disclaimer, the term of this patent is extended or adjusted under 35 U.S.C. 154(b) by 40 days.

(21) Appl. No.: 17/312,769

(22) PCT Filed: Oct. 31, 2019

(86) PCT No.: PCT/CN2019/114681
§ 371 (c)(1),
(2) Date: Jun. 10, 2021

(87) PCT Pub. No.: WO2020/125226
PCT Pub. Date: Jun. 25, 2020

(65) Prior Publication Data
US 2022/0047405 A1 Feb. 17, 2022

(30) Foreign Application Priority Data
Dec. 18, 2018 (CN) .......................... 20181549944.9
Dec. 18, 2018 (CN) .......................... 20181550926.2
(Continued)

(51) Int. Cl.
*A61F 2/89* (2013.01)
*A61F 2/06* (2013.01)
(Continued)

(52) U.S. Cl.
CPC .................. *A61F 2/89* (2013.01); *A61F 2/07* (2013.01); *A61F 2/856* (2013.01);
(Continued)

(58) Field of Classification Search
None
See application file for complete search history.

(56) References Cited

U.S. PATENT DOCUMENTS

| 8,636,789 B2 | 1/2014 | Ivancev |
| 10,219,922 B2 | 3/2019 | Robison |

(Continued)

FOREIGN PATENT DOCUMENTS

| CN | 101283937 A | 10/2008 |
| CN | 102370528 A | 3/2012 |
| CN | 108601648 A | 9/2018 |

OTHER PUBLICATIONS

International Search Report dated Feb. 6, 2020 for corresponding PCT Application No. PCT/CN2019/114681.
(Continued)

*Primary Examiner* — Leslie A Lopez
(74) *Attorney, Agent, or Firm* — Raymond Sun

(57) ABSTRACT

A lumen stent (100) and an implant are provided. The lumen stent includes a tubular body (11), an inner branch (12) and an outer branch (13) which are respectively communicated with the tubular body (11). The tubular body (11) includes a first body segment (111), a tapered segment (112) and a second body segment (113) which are connected in sequence. The tapered segment (112) is provided with an outer branch window (110*b*) and an inner branch window (110*a*). The proximal end of the outer branch (13) is connected to the outer branch window (110*b*). The distal end of the inner branch (12) is connected to the inner branch window (110*a*). The area of the inner branch window (110*a*)
(Continued)

is larger than that of the outer branch window (110b). The beneficial effects are as follows: since the area of the inner branch window (110a) is larger than that of the outer branch window (110b), most of blood flow can rapidly pass through the inner branch (12), so that the blood flow pressure of the outer branch (13) is reduced, and the distal end of the outer branch (13) is prevented from tilting and touching an inner wall of a tumor cavity.

20 Claims, 9 Drawing Sheets

(30) Foreign Application Priority Data

| Dec. 18, 2018 | (CN) | ............................ 201815509328 |
|---|---|---|
| Dec. 18, 2018 | (CN) | ............................ 201815509347 |
| Dec. 18, 2018 | (CN) | ............................ 201815509417 |
| Dec. 18, 2018 | (CN) | ............................ 201815549715 |
| Dec. 18, 2018 | (CN) | ............................ 201815549749 |

(51) Int. Cl.
  *A61F 2/07* (2013.01)
  *A61F 2/856* (2013.01)

(52) U.S. Cl.
  CPC ... *A61F 2002/061* (2013.01); *A61F 2002/065* (2013.01); *A61F 2002/067* (2013.01); *A61F 2220/0016* (2013.01); *A61F 2250/001* (2013.01); *A61F 2250/0039* (2013.01)

(56) References Cited

U.S. PATENT DOCUMENTS

| 11,471,278 | B2 | 10/2022 | Braille et al. | |
|---|---|---|---|---|
| 2003/0176911 | A1* | 9/2003 | Iancea | A61F 2/915 |
| | | | | 623/1.13 |
| 2006/0229707 | A1* | 10/2006 | Khoury | A61F 2/915 |
| | | | | 623/1.35 |
| 2007/0043425 | A1* | 2/2007 | Hartley | A61F 2/07 |
| | | | | 623/1.13 |
| 2009/0319022 | A1* | 12/2009 | Hartley | A61F 2/07 |
| | | | | 623/1.13 |
| 2012/0323303 | A1* | 12/2012 | Ivancev | A61F 2/07 |
| | | | | 623/1.13 |
| 2013/0103132 | A1 | 4/2013 | Madjarov | |
| 2013/0138199 | A1 | 5/2013 | Ivancev | |
| 2014/0094902 | A1* | 4/2014 | Khoury | A61F 2/856 |
| | | | | 623/1.35 |
| 2017/0189212 | A1 | 7/2017 | Eller et al. | |
| 2018/0071078 | A1 | 3/2018 | Majolagbe | |
| 2020/0383769 | A1 | 12/2020 | Xiao | |

OTHER PUBLICATIONS

Office Action for corresponding China Application No. 201811549944.9.
Office Action for corresponding China Application No. 201811550926.2.
Office Action for corresponding China Application No. 201811550934.7.
First Office Action for corresponding China Application No. 201811550941.7.
Office Action for corresponding China Application No. 201811554971.5.
Office Action for corresponding China Application No. 201811550932.8.
Office Action for corresponding China Application No. 201811554974.9 dated Nov. 26, 2020.
Second Office Action for corresponding China Application No. 201811550941.7.
Office Action dated Nov. 4, 2020 for corresponding China Application No. 201811550932.8.
Notice of Grant dated Jun. 1, 2021 for corresponding China Application No. 201811550932.8.
Search Report dated Oct. 25, 2022 for corresponding European Application No. EP 19 89 7825.
Office Action dated Mar. 31, 2022 for corresponding India Application No. 202127032150.
Written Opinion dated Oct. 25, 2022 for corresponding European Application No. EP 19 89 7825.

* cited by examiner

LUMEN STENT AND IMPLANT

FIELD

The application relates to the technical field of interventional medical instruments, and more particularly, relates to a lumen stent and an implant.

BACKGROUND

Over the past decade, endovascular stent-graft exclusion has been widely used in the treatment of thoracic and abdominal aortic aneurysms, aortic dissegments and other lesions, and has been the first-line treatment with definite efficacy, less trauma, rapid recovery and fewer complications. During operation, under X-ray fluoroscopy monitoring, a covered stent is conveyed to a lesion position through a corresponding delivery system, the covered stent isolates blood flow from the lesion position, the influence of blood pressure on the lesion position is eliminated, and the therapeutic effect is achieved.

However, the vascular structure of a human body is complex, and there are many side branches. Meanwhile, the individual difference between patients is large, a tumor body may be long, and the positional difference of a tumor body may also be large. Clinically, the situation that a tumor body is located at side branch vessels, or near side branches, is also common. If the release position of the covered stent is not accurate, the side branch vessels are often occluded. Standardized straight-tube covered stents on the market find it difficult to meet the requirements of different anatomical structures for the treatment of lesions, and it is often necessary to customize side branch vessels to specific vascular sites. However, the customized multi-branch stent is expensive and has a long manufacturing cycle, which makes it difficult for emergency patients to wait, and also has a small indication range.

SUMMARY

The present invention provides a lumen stent and an implant aimed at addressing the defects described in the background.

The technical scheme adopted by the application for solving the technical problem is as follows.

A lumen stent is provided. The lumen stent includes a tubular body, and an inner branch and an outer branch which are respectively communicated with the tubular body. The tubular body includes a first body segment, a tapered segment and a second body segment which are connected in sequence. The tapered segment is provided with an outer branch window and an inner branch window. The proximal end of the outer branch is connected to the outer branch window. The distal end of the inner branch is connected to the inner branch window. The area of the inner branch window is larger than that of the outer branch window.

Another lumen stent is provided. The lumen stent includes a tubular body, two inner branches and two outer branches which are respectively communicated with the tubular body, and an imaging mark for positioning the inner branches and the outer branches. The tubular body includes a first body segment, a tapered segment and a second body segment which are connected in sequence. The distal end of the inner branch is connected to the tapered segment. The proximal end of the outer branch is connected to the tapered segment. The two inner branches are located between the two outer branches. An angle between the inner branch and the adjacent outer branch in a circumferential direction is between 60-80°. An angle between the two outer branches in the circumferential direction is between 170-180°.

Yet another lumen stent is provided. The lumen stent includes a tubular body, and an inner branch and an outer branch which are communicated with the tubular body respectively. The tubular body includes a first body segment, a tapered segment and a second body segment which are connected in sequence. The distal end of the inner branch is connected to the tapered segment. The proximal end of the outer branch is connected to the tapered segment. A distal waveform ring of the inner branch is located above a proximal waveform ring of the outer branch.

A further stent is provided. The lumen stent includes a tubular body, and an inner branch and an outer branch which are respectively communicated with the tubular body. The tubular body includes a first body segment, a tapered segment and a second body segment which are connected in sequence. The distal end of the inner branch is connected to the tapered segment. The proximal end of the outer branch is connected to the tapered segment. The distal end of the inner branch is located above the proximal end of the outer branch.

An implant is provided. The implant includes a tubular body and a partial-release device connected to an outer surface of the tubular body. The partial-release device includes a limiting rod and a binding unit movably connected to the limiting rod. The binding unit includes a binding wire, a lock catch assembly and at least one limiting ring buckle. The lock catch assembly is connected to the binding wire. The limiting ring buckle is fixed on the tubular body. The binding wire and/or the lock catch assembly penetrate from one side of the limiting ring buckle to the other side. When the limiting rod penetrates into the lock catch assembly, the binding wire restrains the tubular body circumferentially.

Another implant is provided. The implant includes a tubular body and a partial-release device connected to an outer surface of the tubular body. The partial-release device includes a limiting rod and a binding unit movably connected to the limiting rod. The tubular body includes a first region and a second region in a circumferential direction. The binding unit is disposed in the second region. The binding unit includes a binding wire and a lock catch assembly connected to the binding wire. When the limiting rod penetrates into the lock catch assembly, the binding wire restrains the tubular body circumferentially.

Yet another implant is provided. The implant includes a tubular body and a partial-release device connected to an outer surface of the tubular body. The partial-release device includes a limiting rod and a plurality of binding units movably connected to the limiting rod. The binding unit includes a binding wire and a lock catch assembly. The binding wire includes a fixing portion fixedly connected to the tubular body, and two binding portions respectively extending from both sides of the fixing portion. The lock catch assembly is respectively connected to the two binding portions. When the limiting rod penetrates into the lock catch assembly, the binding wire restrains the tubular body circumferentially.

In conclusion, a lumen stent and an implant of the application have the following beneficial effects: according to the present application, the inner branch and the outer branch are disposed on the tapered segment of the lumen stent, and since the tapered segment is closer to the first body segment than the second body segment, a guide wire has more operation space after passing out from the distal end of the inner branch or the outer branch, so that the guide wire is conveniently and accurately introduced into a branch vessel, thereby enlarging the indication range. Moreover, since the area of the inner branch window is larger than that of the outer branch window, most of blood flow can rapidly pass through the inner branch, so that the blood flow pressure of the outer branch is reduced, and the distal end of the outer branch is prevented from tilting and touching an inner wall of a tumor cavity.

BRIEF DESCRIPTION OF THE DRAWINGS

The present invention will now be further described by way of embodiments with reference to the accompanying drawings, where.

DETAILED DESCRIPTION OF THE EMBODIMENTS

In order that the above objects, features, and advantages of the application can be more readily understood, specific implementations of the application will be described below in detail with reference to the accompanying drawings. In the following description, numerous specific details are set forth in order to provide a thorough understanding of the application. The application may, however, be embodied in many different forms than those herein set forth, and such modifications as would occur to those skilled in the art may be made without departing from the spirit and scope of the application.

It will be understood that when an element is referred to as being "fixed" or "arranged" to another element, it may be directly on another element or centered elements may also be present. When an element is referred to as being "connected" to another element, it may be directly connected to another element or centered elements may also be present. The terms "vertical", "horizontal", "left", "right" and the like as used herein are for illustrative purposes only and are not meant to be the only implementations.

Unless defined otherwise, all technical and scientific terms used herein have the same meaning as commonly understood by those skilled in the art to which the application belongs. The terms used in the description of the application herein are for the purpose of describing specific implementations only and are not intended to be limiting of the application. The term "and/or" as used herein includes any and all combinations of one or more of the associated listed items.

In the field of interventional medical treatment, it is common to define an end of an implant (e.g. a lumen stent) proximal to the heart after released as a proximal end and an end distal to the heart as a distal end.

Figure 1:
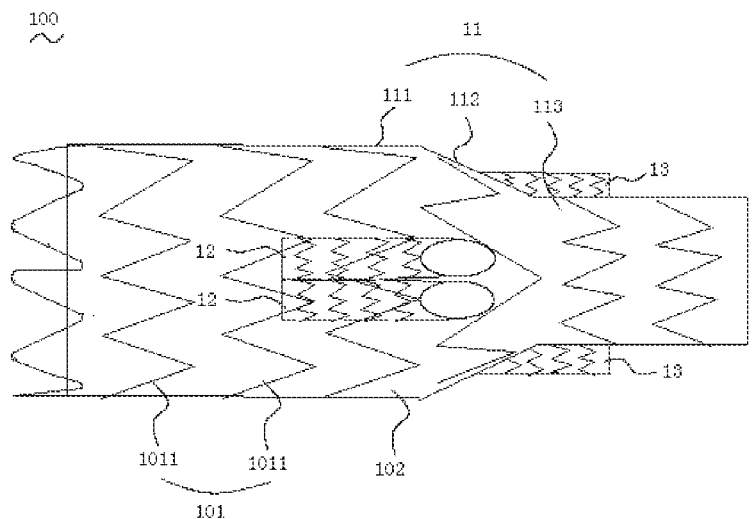
FIG. 1 is a schematic diagram of a lumen stent according to a first embodiment of the application.

Referring to FIG. 1, a first embodiment of the present application provides a lumen stent 100, which includes a tubular body 11 and two inner branches 12 and two outer branches 13 respectively communicating with the tubular body 11. The tubular body 11, the inner branches 12 and the outer branches 13 are covered stents, each having a hollow lumen that constitutes a passage for blood flow circulation.

The covered stent includes a bare stent 101 and a covering film 102 connected to the bare stent 101. The bare stent 101 is made of a material with good biocompatibility, such as nickel titanium and stainless steel. The covering film 102 is made of a polymer material having good biocompatibility, such as PTFE, FEP and PET. The bare stent 101 includes a plurality of waveform rings 1011. The plurality of waveform rings 1011 are arranged in sequence, such as at intervals in parallel, from the proximal end to the distal end. The waveform ring 1011 is a closed cylindrical structure, and the plurality of waveform rings 1011 may have the same or similar waveform shape. For example, the waveform ring 1011 may be a Z-wave, M-wave, V-wave and sinusoidal wave structure, or another structure that may be radially compressed to a very small diameter, etc. It is to be understood that the present embodiment does not limit the specific structure of the waveform ring 1011; waveforms of the waveform ring 1011 may be set as required, and the number of the waveforms in each waveform ring 1011 and the height of the waveforms may be set as required. In actual preparation, the bare stent 101 may be formed by cutting and shaping a nickel-titanium tube, and then the bare stent 101 is sutured on the covering film 102.

The tubular body 11 includes a first body segment 111, a tapered segment 112 and a second body segment 113 which are connected in sequence. The cross-section area of the first body segment 111 is larger than that of the second body segment 113. The two inner branches 12 and the two outer branches 13 are respectively connected to the tapered segment 112. The distal end of the inner branch 12 is fixed on the tapered segment 112, and the proximal end is located inside the tubular body 11 and extends towards a side away from the second body segment 113. The proximal end of the outer branch 13 is fixed on the tapered segment 112, and the distal end is located outside the tubular body 11 and extends towards a side away from the first body segment 111.

Figure 2:
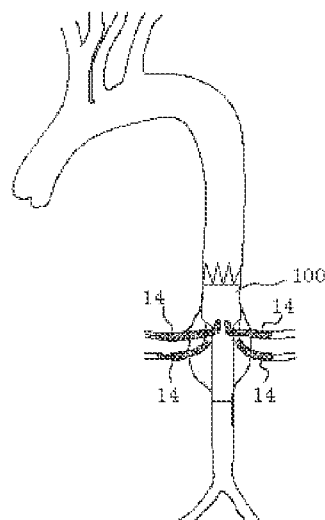
FIG. 2 is a schematic diagram of the lumen stent of FIG. 1 placed within a tumor cavity.

Referring to FIG. 1 and FIG. 2, during deployment, the first body segment 111 is first attached to a healthy vessel wall upstream of a tumor cavity, and the tapered segment 112 and the second body segment 113 are retained within the tumor cavity. Subsequently, a guide wire (not shown) passes through the inner branch 12 or the outer branch 13 and is introduced into a branch vessel near the tumor cavity to establish a track. Then, one end of an elongated stent 14 is inserted into the inner branch 12 or the outer branch 13, the other end of the elongated stent 14 is located in the branch vessel, and blood flow passing from the tubular body 11 is introduced into the branch vessel through the elongated stent 14.

According to the present application, the two inner branches 12 and the two outer branches 13 are connected to the tapered segment 112. Since the tapered segment 112 is closer to the first body segment 111 than the second body segment 113, the guide wire has more operation space after passing out from the distal end of the inner branch 12 or the outer branch 13, so that the guide wire is conveniently and accurately introduced into the branch vessel. Moreover, by arranging the two inner branches 12 and the two outer branches 13 on the tapered segment 112, the distal ends of the inner branches 12 and the outer branches 13 may be located in different planes, so that the elongated stents 14 are arranged in a staggered manner in the tumor cavity, and extrusion between the elongated stents 14 is avoided.

Since the lumen stent 100 further includes imaging marks (not shown) for positioning the inner branches 12 and the outer branches 13, if the two outer branches 13 are spaced too close to each other, the imaging marks of the two outer branches will interfere, which is unfavorable for the guide wire to be selected into the corresponding branch, influences the operation, and prolongs the operation time; for example, the two outer branches are spaced away from each other. In the same way, if one inner branch 12 is spaced too close to the adjacent outer branch 13, the guide wire is influenced to be selected into the outer branch 13 after the elongated stent surrounding the inner branch is first connected, and the imaging marks of the inner and outer branches will also interfere; for example, the inner and outer branches are spaced away from each other. If the two inner branches are symmetrically spaced from the two outer branches, the imaging marks of the two inner branches easily interfere under a planar perspective image, so that the two inner branches 12 are located between the two outer branches 13. Therefore, it is necessary to rationally design the position between the inner branches 12 and the outer branches 13, to avoid interference of imaging marks between the four branches, and to avoid influence on the selection of the guide wire due to the fact that the branches are spaced too close to each other. In the present application, the two inner branches 12 are located between the two outer branches 13, an angle a between one inner branch 12 and the adjacent outer branch 13 in a circumferential direction is between 60°-80°, and an angle b between the two outer branches 13 in the circumferential direction is between 170°-180°.

Figure 3:
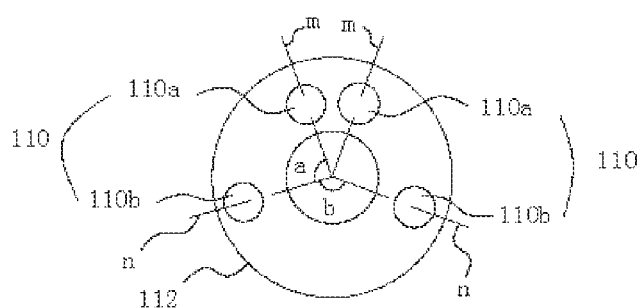
FIG. 3 is a schematic diagram of the same area of four windows on a tapered segment of the lumen stent of FIG. 1.

Referring to FIG. 3, the tubular body 11 is provided with four windows 110, two of which are inner branch windows 110a connected to the inner branches 12 and the other two of which are outer branch windows 110b connected to the outer branches 13, and imaging marks (not shown) are disposed at the edges of the four windows 110 or near the four windows. It is to be noted that a plane passing through the geometric center of the inner branch window 110a and passing through a longitudinal center axis of the tapered segment 112 is defined as a first plane m, and a plane passing through the geometric center of the outer branch window 110b and passing through the longitudinal center axis of the tapered segment 112 is defined as a second plane n. Here, "the angle a between one inner branch 12 and the adjacent outer branch 13 in the circumferential direction" refers to an angle a between the first plane m and the adjacent second plane n, and "the angle b between the two outer branches 13 in the circumferential direction" refers to an angle b between the two second planes n. It is to be understood that the present embodiment does not limit the specific structure and the connection position of a developing structure as long as the positioning of the window 110 can be achieved. For example, the developing structure is an elastic metal ring having a developing function connected to a peripheral outer edge of the window 110.

Figure 4:
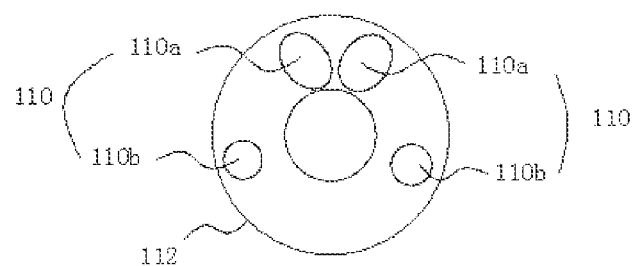
FIG. 4 is a schematic diagram of the tapered segment of the lumen stent of FIG. 1 with an inner branch window having a larger area than an outer branch window.

In the embodiment shown in FIG. 3, the four windows 110 have the same area. It is to be understood that the four windows 110 may also have different areas in other embodiments. For example, in the embodiment shown in FIG. 4, the area of the inner branch window 110a is larger than that of the outer branch window 110b. After the inner branch 12 and the outer branch 13 of the lumen stent are released, since the distal end of the outer branch 13 is a free end, under the impact of blood flow, the distal end of the outer branch 13 may tilt upwards and even touch the inner wall of the tumor cavity to stimulate the blood vessel. Since the area of the inner branch window 110a is larger than that of the outer branch window 110b, most of blood flow can rapidly pass through the inner branch 12, so that the blood flow pressure of the outer branch 13 is reduced, and the distal end of the outer branch 13 is prevented from tilting and touching the inner wall of the tumor cavity.

It is to be understood that a middle portion of the outer branch 13 may be fixed to the tubular body 11 at a point connection in order to avoid tilting of the distal end of the outer branch 13 to touch the inner wall of the tumor cavity, while preventing the operative space from being too small after the guide wire has passed out from the distal end of the outer branch 13.

Figure 5:
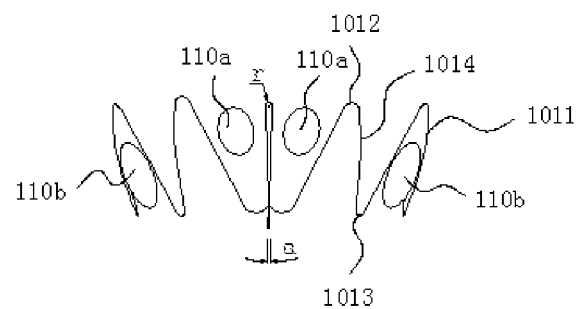
FIG. 5 is a schematic diagram of a waveform ring of the tapered segment of the lumen stent of FIG. 1.

Referring to FIG. 5, the tapered segment is provided with a waveform ring 1011 that includes a plurality of peaks 1012, a plurality of valleys 1013 and a plurality of connecting rods 1014 respectively connecting the adjacent peaks 1012 and valleys 1013. The waveform ring 1011 has a supporting effect on a peripheral structure thereof. If the proximal end of the outer branch 13 is connected above the valley 1013, the valley 1013 will have an upward supporting force on the proximal end of the outer branch 13. Since the distal end of the outer branch 13 is a free end, the supporting force will cause the distal end of the outer branch 13 to tilt upwards and even touch the inner wall of the tumor cavity. If the proximal end of the outer branch 13 is connected below the peak 1012, the peak 1012 has a downward supporting force on the lower end of the outer branch 13, so that the longitudinal center axis of the outer branch 13 is substantially parallel to the longitudinal center axis of the tubular body 11, thereby preventing the distal end of the outer branch 13 from tilting outwards to touch the inner wall of the tumor cavity. Therefore, in the present embodiment, the proximal end of the outer branch 13 is connected below the peak 1012. Also, if the distal end of the inner branch 12 is connected below the peak 1012 due to the supporting action of the waveform ring 1011, the peak 1012 limits an upward bending angle of the elongated stent 14 retained in the inner branch 12, and the elongated stent 14 is folded when the upward bending angle of the elongated stent 14 is too large. Therefore, in the present embodiment, the distal end of the inner branch 12 is connected above the valley 1013 to facilitate connection of the elongate stent 14.

Further, at least one peak 1012 and at least one valley 1013 are disposed between one inner branch window 110a and the adjacent outer branch window 110b to ensure that the proximal end of outer branch 13 is connected below the peak 1012 and the distal end of inner branch 12 is connected above the valley 1013. For example, only one peak 1012 and one valley 1013 are disposed between one inner branch window 110a and the adjacent outer branch window 110b to reduce the overall sheathing volume of the lumen stent.

Referring again to FIG. 2, since there is a plurality of elongated stents 14, in order to avoid interference between the elongated stents 14, the elongated stents 14 on a pair of adjacent inner branch 12 and outer branch 13 are generally bent towards one side, and the elongated stents 14 on the other pair of adjacent inner branch 12 and outer branch 13 are bent towards the other side. That is, the elongated stents 14 retained in the adjacent inner branch 12 and outer branch 13 easily interfere, and the angle a of the adjacent inner and outer branches in the circumferential direction needs to be increased. It is to be understood that under the condition that the arrangement of the inner and outer branches meets the above angle requirements, the angle between the two inner branches 12 in the circumferential direction will need to be reduced if the angle of the adjacent inner and outer branches in the circumferential direction is to be increased.

In the embodiment shown in FIG. 5, a peak 1012 is disposed between the two inner branch windows 110a. The peak 1012 not only supports the inner branch window 110a to avoid recessing the distal end of the inner branch, but also ensures that the two inner branch windows 110a are located above the valley 1013. Further, in order to prevent the two inner branch windows 110a from being too far apart, the waveform angle a of the peak 1012 is between 0-10°. It is to be noted that "waveform angle α" here refers to an angle between the connecting rods 1014 connected to both sides of the peak 1012, and when the waveform angle is 0, the connecting rods 1014 on both sides of the peak 1012 are disposed in parallel. If the fillet radius r at the peak 1012 or the valley 1013 is too large, the stent is not easily compressed, and the overall sheathing volume of the stent is affected, but if the fillet radius r is too small, the vessel stimulation by the peak 1012 or the valley 1013 becomes large. Therefore, the fillet radius r of the peak 1012 and/or the valley 1013 of the waveform ring 1011 on the tapered segment 112 is between 0.5-1.5 mm.

Figure 6:
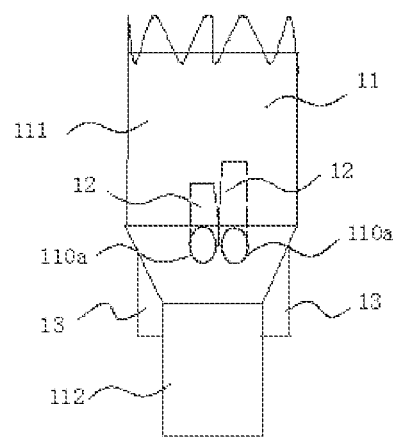
FIG. 6 is a schematic diagram of a closed connection between the distal end of an inner branch of the lumen stent of FIG. 1 and a tubular body.

Referring to FIG. 6, the distal end of each inner branch 12 is fixed on the inner branch window 110a with the proximal end extending towards a side away from the second body segment 113 and, in order to prevent the inner branch 12 from swinging under the impact of blood flow, the inner branch 12 may be fixed on the tubular body 11 to facilitate the selection of the guide wire into the corresponding inner branch 12.

Due to a certain distance between the two inner branch windows 110a, a gap is formed between the outer walls of the two inner branches 12 and the inner wall of the tubular body 11. The gap easily leads to thrombus formation. Therefore, in order to avoid the thrombus moving along the gap to the downstream blood vessel, the outer walls of the distal ends of the two inner branches 12 are in closed connection with the inner wall of the tubular body 11; i.e., there is no gap between the outer walls of the distal ends of the two inner branches 12 and the inner wall of the tubular body 11. Specifically, the distal ends of the two inner branches 12 may be fixed together by suture, and then the distal ends of the two inner branches 12 may be fixed on the inner wall of the tubular body 11. Further, in order to avoid thrombus formation, the entire outer wall of the two inner branches 12 is in closed connection with the tubular body 11.

Figure 7:
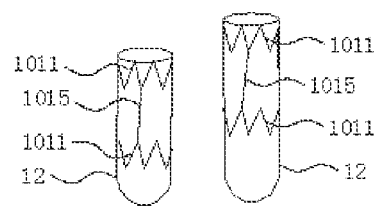
FIG. 7 is a schematic diagram of a supporting rod disposed on the inner branch of the lumen stent of FIG. 6.
Figure 8:
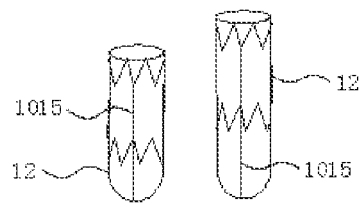
FIG. 8 is a schematic diagram of the supporting rod of FIG. 7 extending to the distal end of the inner branch.

In the embodiment shown in FIG. 7, the two inner branches 12 have different heights, and the waveform rings 1011 on the two inner branches 12 are distributed in a staggered manner to reduce the overall sheathing volume of the first body segment 111. Moreover, at least one supporting rod 1015 is disposed on the inner branch 12 to increase an axial supporting force of the inner branch 12. Both ends of the supporting rod 1015 may be connected to the adjacent two waveform rings 1011 respectively, and the supporting rod 1015 may be parallel to the longitudinal center axis of the inner branch 12 or may be inclined with respect to the longitudinal center axis of the inner branch 12. For example, the supporting rods 1015, the longitudinal center axis of the inner branch 12 and the longitudinal center axis of the first body segment 111 are coplanar, and at this moment, the supporting rod 1015 has the best axial supporting effect. In the embodiment shown in FIG. 8, the supporting rod 1015 extends to the distal end of the inner branch 12 to avoid collapse of a covered region at the distal end of the inner branch 12, to facilitate selection of the guide wire into the inner branch 12 and to facilitate connection of the elongated stent.

Figure 9:
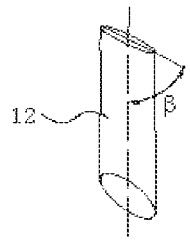
FIG. 9 is a schematic diagram of the inclined arrangement of a proximal end surface of the inner branch of FIG. 1.

Referring to FIG. 9, in order to facilitate selection of the guide wire into the inner branch 12, the proximal end surface of the inner branch 12 is inclined with respect to the longitudinal center axis of the inner branch 12. It is to be understood that as an angle β between the proximal end surface of the inner branch 12 and the longitudinal center axis thereof is smaller, it is more favorable for the guide wire to be selected into the inner branch 12, but if the angle β is too small, the connection strength of the elongated stent and the inner branch 12 will be affected. Therefore, in the present embodiment, the angle β between the proximal end surface of the inner branch 12 and the longitudinal center axis of the inner branch 12 is between 30°-60°. For example, the lowest point of the proximal end surface of the inner branch 12 is located in a plane formed by the longitudinal center axis of the inner branch 12 and the longitudinal center axis of the first body segment 111 in order to facilitate selection of the guide wire.

Figure 10:
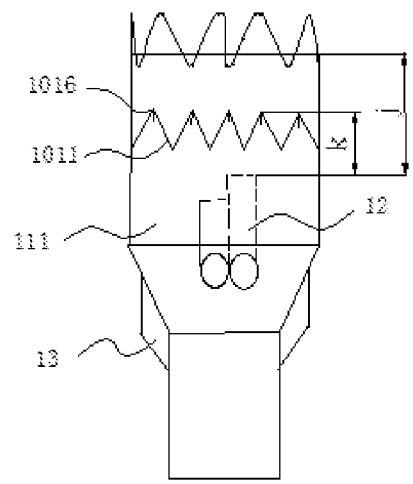
FIG. 10 is a schematic diagram of a barbed structure disposed on the lumen stent of FIG. 1.

Referring to FIG. 10, a vertical distance j between the highest point of the proximal end surface of the inner branch 12 and the proximal end of the first body segment 111 is not less than 20 mm. At this moment, when the proximal end of the first body segment 111 needs to be coupled with another stent (not shown), the difference of the distance between the highest point of the proximal end surface of the inner branch 12 and the proximal end of the first body segment 111 may provide a sufficient anchoring region for other coupled stents, thereby preventing the other coupled stents from interfering with the inner branch 12.

Further, the outer wall of the first body segment 111 is provided with a barbed structure 1016 to enhance the overall anchoring performance of the lumen stent. When another stent is coupled to surround the outside the proximal end of the first body segment 111, if the barbed structure 1016 is too close to the proximal end of the first body segment 111, the barbed structure 1016 may easily pierce the another stent to create an internal leakage. However, if the barbed structure 1016 is too close to the internal branch 12, the overall smoothness of the lumen stent may be influenced. Therefore, the barbed structure 1016 is fixed on the outer wall of the first body segment 111 and is located between the proximal end of the inner branch 12 and the proximal end of the first body segment 111. In the embodiment shown in FIG. 10, the barbed structure 1016 is disposed on the waveform ring 1011 of the first body segment 111 such that a vertical distance k between the highest point of the proximal end surface of the inner branch 12 and the barbed structure 1016 is about 5-15 mm.

Figure 11:
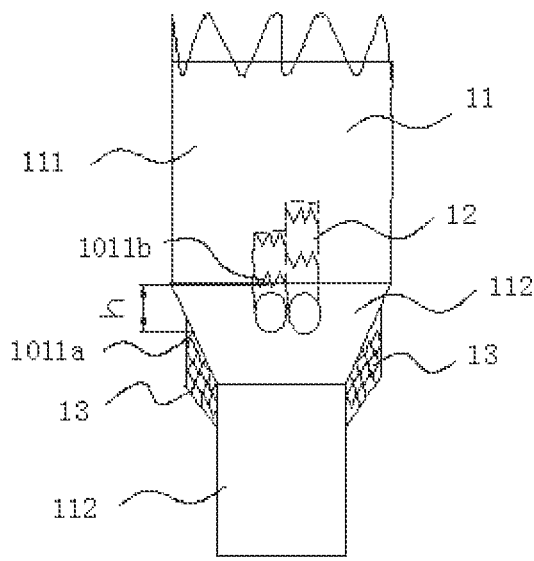
FIG. 11 is a schematic diagram of a distal waveform ring of the inner branch of the lumen stent of FIG. 1 located above a proximal waveform ring of an outer branch.

Referring to FIG. 11, the proximal end of the outer branch 13 is fixed on the outer branch window and the other end extends towards a side away from the first body segment 111. Since both the inner and outer branches are disposed on the tapered segment 112, in order to reduce the sheathing volume of the tapered segment 112, in the present embodiment, the distal waveform ring 1011$b$ of the inner branch 12 is located above the proximal waveform ring 1011$a$ of the outer branch 13, i.e. a vertical distance h between the peak of the proximal waveform ring 1011$a$ of the outer branch 13 and the valley of the distal waveform ring 1011$b$ of the inner branch 12 is more than or equal to 0. However, when the value of h is too large, the distal waveform ring 1011$b$ is too far from the distal end of the inner branch 12 or the proximal waveform ring 1011$a$ is too far from the proximal end of the outer branch 13, which easily causes the distal end of the inner branch 12 or the proximal end of the outer branch 13 to collapse. Therefore, the value of h is not more than 15 mm.

Figure 12:
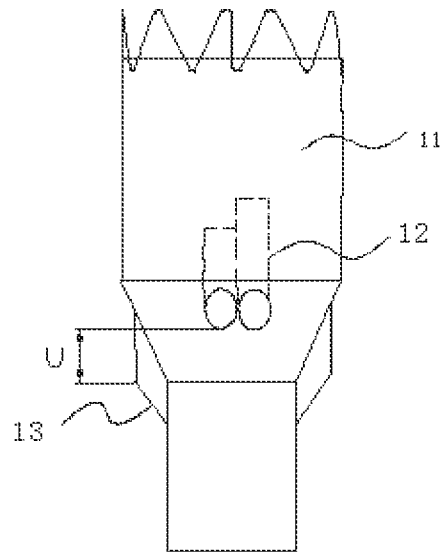
FIG. 12 is a schematic diagram of the distal end of the inner branch of the lumen stent of FIG. 1 located above the distal end of the outer branch.

In the embodiment shown in FIG. 12, the distal end of the inner branch 12 is located above the distal end of the outer branch 13; i.e., a vertical distance c between the highest point on the distal end surface of the outer branch 13 and the lowest point on the distal end surface of the inner branch 12 is more than 0 to ensure that the outer branch 13 remains within a delivery sheath when the distal end of the inner branch 12 is just released from the delivery sheath. In the process of releasing the stent, the stent is subjected to high blood flow pressure, so that the accurate positioning of the stent is not facilitated. When the distal end of the inner branch 12 is just released from the delivery sheath and the outer branch 13 remains within the delivery sheath, the blood flow can rapidly pass through the inner branch 12, the impact of the blood flow on a stent system is reduced, the positioning of the inner branch 12 is facilitated, and the subsequent release process can be more stable. It is to be understood that if the value of c is too small, it is easy to release the inner branch 12 and the outer branch 13 simultaneously during operation, which is unfavorable for the positioning of the stent. Moreover, if the value of c is too large, the outer branch 13 is too long, so that there is insufficient operation space for the guide wire after it passes out from the distal end of the outer branch 13, the guide wire cannot be accurately introduced into the branch vessel, and the operation time is prolonged. Therefore, the value of c is not less than 5 mm and not more than 12 mm.

Further, the distal end surface of the outer branch 13 is inclined with respect to the longitudinal center axis of the outer branch 13. It is to be understood that as the angle between the distal end surface of the outer branch 13 and the longitudinal center axis thereof is smaller, the guide wire has more operation space after passing out from the distal end of the outer branch 13 to facilitate accurate introduction of the guide wire into the branch vessel, but if the angle is too small, the connection strength of the elongated stent and the outer branch 13 will be influenced. Therefore, in the present embodiment, the angle between the distal end surface of the outer branch 13 and the longitudinal center axis of the outer branch 13 is about 30°-60°.

Figure 13:
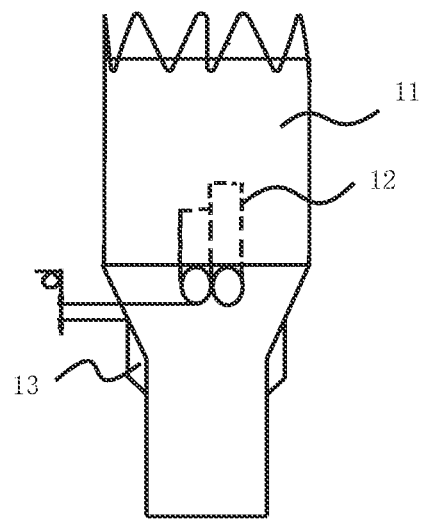
FIG. 13 is a schematic diagram of the distal end of the inner branch of the lumen stent of FIG. 1 located above the proximal end of the outer branch.

In the embodiment shown in FIG. 13, the distal end of the inner branch 12 is located above the proximal end of the outer branch 13; i.e., a vertical distance d between the highest point on the proximal end surface of the outer branch 13 and the lowest point on the distal end surface of the inner branch 12 is more than 0. Since the distal end of the inner branch 12 is located above the proximal end of the outer branch 13, there is no overlap between the inner branch 12 and the outer branch 13 in an axial direction, which not only reduces the sheathing volume of the tapered segment, but also ensures that when the distal end of the inner branch 12 is just released from the delivery sheath, the outer branch 13 remains within the delivery sheath, facilitating the positioning of the inner branch 12 and making the subsequent release process more stable. However, if the value of d is too large, the outer branch 13 would be too long, so that the operation space of the guide wire after the guide wire passes out from the distal end of the outer branch 13 is insufficient, the guide wire cannot be accurately introduced into the branch vessel, and the operation time is prolonged. Therefore, the value of d is not more than 10 mm.

The present application also provides an implant that may be contained within a delivery sheath in a compressed state and automatically return to a predetermined form upon release from the delivery sheath. The implant may be a product such as a lumen stent, a valve, an occluder or a filter.

Figure 14:
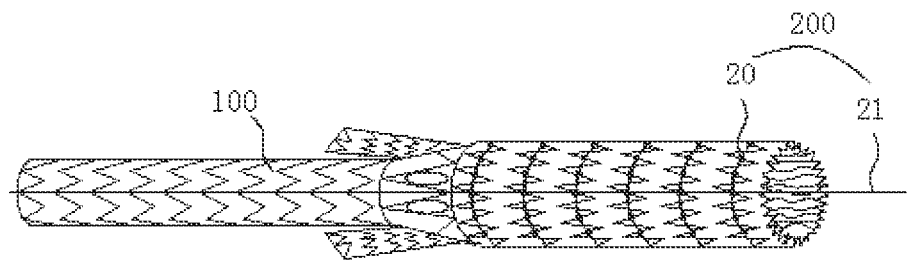
FIG. 14 is a schematic diagram of a lumen stent according to a second exemplary embodiment of the application in a partial-release state.

Referring to FIG. 14, a second exemplary embodiment of the present application provides an implant which is a lumen stent. The second embodiment is substantially the same as the first embodiment except that an outer surface of the lumen stent 100 is provided with a partial-release device 200 to accurately position the lumen stent 100.

Since the lumen stent 100 is primarily positioned axially and circumferentially using imaging marks thereon, when the lumen stent 100 is compressed within the delivery sheath, the lumen stent 100 has a compression fold in the circumferential direction and is in an elongated state in the axial direction. If the lumen stent 100 is positioned by the imaging marks at this moment, large circumferential and axial deviations will occur. According to the present application, the outer surface of the lumen stent 100 is provided with the partial-release device 200. When the lumen stent 100 is completely released from the delivery sheath, the lumen stent 100 is in a partial-release state under the restraint of the partial-release device 200. At this moment, the lumen stent 100 is not attached to the wall of the blood vessel, and an operator can still adjust the axial and circumferential positions of the lumen stent 100 to be positioned accurately, the restraint of the partial-release device 200 is relieved, and the lumen stent 100 is expanded and attached to the wall.

It is to be understood that if a cross-section circumscribed circle diameter of the lumen stent 100 is too large when the lumen stent is in a partial-release state, the stent is easily attached to the wall and is unfavorable to axial and circumferential adjustment thereof. If the cross-section circumscribed circle diameter of the lumen stent 100 is too small when the lumen stent is in the partial-release state, the effect of partial-release is not large, and there is still a large circumferential and axial positioning deviation. Therefore, in the present embodiment a ratio of the cross-section circumscribed circle diameter of the lumen stent 100 in the partial-release state to the cross-section circumscribed circle diameter of the expanded lumen stent 100 is 0.6-0.8.

Figure 15:
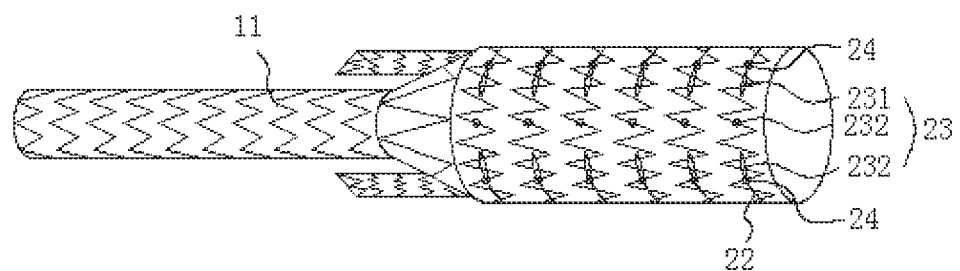
FIG. 15 is a schematic diagram of the lumen stent of FIG. 14 when fully expanded.

Referring to FIG. 14 and FIG. 15, the partial-release device 200 includes a limiting rod 21 and a plurality of binding units 20 for circumferentially restraining the lumen stent 100. The limiting rod 21 is movably retained inside in the binding units 20. The binding unit 20 includes a binding wire 22, a lock catch assembly 23 and at least one limiting ring buckle 24. The limiting ring buckle 24 is fixed on the tubular body 11. The binding wire 22 and/or the lock catch assembly 23 penetrate from one side of the limiting ring buckle 24 to the other side. When the limiting rod 21 is inserted through the lock catch assembly 23, the binding wire 22 circumferentially restrains the tubular body 10 nearby. Specifically, the lock catch assembly 23 includes a first lock catch 231 connected to the binding wire 22 and a second lock catch 232 connected to the binding wire 22 and/or the tubular body 11. The limiting rod 21 is movably connected within the first lock catch 231 and the second lock catch 232.

In the embodiment shown in FIG. 14 and FIG. 15, the plurality of binding units 20 are uniformly distributed on the outer surface of the tubular body 11, and each binding unit 20 is distributed in a circumferential direction. Two second lock catches 232 are included. One of the second lock catches 232 is disposed at one end of the binding wire 22, and the other second lock catch 232 is disposed on the tubular body 11. The first lock catch 231 is disposed at the other end of the binding wire 22. The first lock catch 231 and the second lock catches 232 are annular structures. During assembly, the limiting rod 21 is inserted through the first lock catch 231 and the two second lock catches 232 respectively, and after being accurately positioned, the limiting rod 21 is pulled out from the first lock catch 231 and the two second lock catches 232 so as to relieve the restraint. It is to be understood that the present embodiment does not limit the number of the second lock catches 232. For example, in other embodiments, only one second lock catch 232 is included, which is disposed on the binding wire 22 or the tubular body 11. It is also to be understood that the present embodiment does not limit the specific position of the first lock catch 231 or the second lock catch 232 on the binding wire 22, and in other embodiments, the first lock catch 231 or the second lock catch 232 may be located in other regions outside the end of the binding wire 22.

In the present application, the plurality of limiting ring buckles 24 are disposed on the outer surface of the tubular body 11, and the binding wire 22 and/or the lock catch assembly 23 penetrate through the limiting ring buckles 24, so that the binding wire 22 can uniformly compress the tubular body 11, thereby improving the overall positioning accuracy of the stent. Moreover, when the lumen stent 100 is compressed within the delivery sheath or the restraint of the binding wire 22 on the lumen stent 100 is relieved, the limiting ring buckle 24 also prevents axial displacement of the binding wire 22 penetrating therein.

Figure 16:
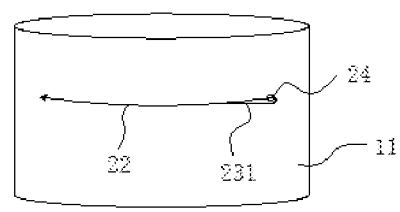
FIG. 16 is a schematic diagram of a first lock catch of the lumen stent of FIG. 14 in a ring structure.

It is to be understood that in other embodiments, the lock catch assembly 23 penetrates from one side of the limiting ring buckle 24 to the other side. For example, in the embodiment shown in FIG. 16, the first lock catch 231 is of an annular structure, and is connected to one end of the binding wire 22, and the first lock catch 231 is retained within the limiting ring buckle 24.

Figure 17:
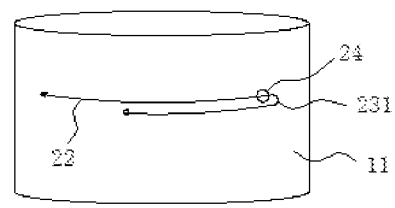
FIG. 17 is a schematic diagram of the first lock catch of the lumen stent of FIG. 14 in a non-ring structure.

It is also to be understood that the present embodiment does not limit the specific structure of the first and second lock catches 231 and 232 as long as the limiting rod 21 is movably connected within the first and second lock catches 231 and 232. For example, in the embodiment shown in FIG. 17, the first lock catch 231 is not of a closed annular structure, and the first lock catch 231 is hooked on the limiting ring buckle 24; i.e., the first lock catch 231 is folded in a reverse direction after penetrating from one side to the other side of the limiting ring buckle 24. At this moment, the binding wire 22 and the first lock catch 231 are of an integrated structure.

Figure 18:
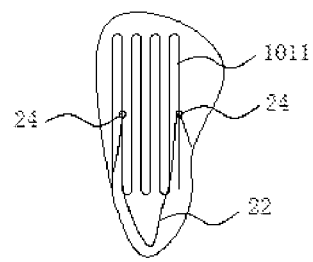
FIG. 18 is a schematic diagram of a binding wire on the lumen stent of FIG. 14 passing over a valley.

It is also to be understood that if the number of the limiting ring buckles 24 is too small, the spacing between two adjacent limiting ring buckles 24 will be too long. When the restraint of the partial-release device 200 is relieved, a region between the two limiting ring buckles 24 of the lumen stent 100 will tend to be depressed, making the stent in this region unable to be expanded and attached to the wall. Moreover, as shown in FIG. 18, if the spacing between the two limiting ring buckles 24 is too long, when the lumen stent 100 is in a radially compressed state, the binding wire 22 between the two limiting ring buckles 24 is axially displaced and even passes over the valley of the waveform ring 101 and is hooked on the valley, so that the stent cannot be normally expanded.

Figure 19:
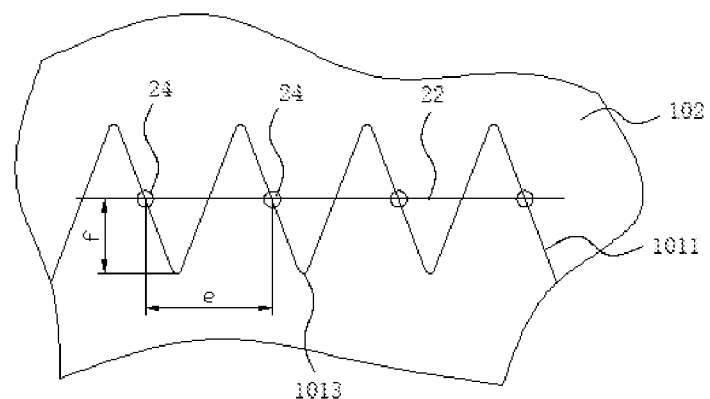
FIG. 19 is a schematic diagram of a limiting ring buckle on the lumen stent of FIG. 14.
Figure 20:
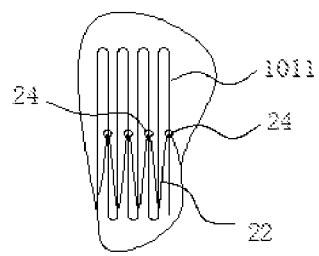
FIG. 20 is a schematic diagram of the binding wire on the lumen stent of FIG. 14 not passing over the valley.

Referring to FIG. 19 and FIG. 20, a linear distance between every two adjacent limiting ring buckles 24 is e, a vertical distance between a fixed point of the limiting ring buckle 24 and a valley 1013 located below the limiting ring buckle 24 and closest to the limiting ring buckle 24 is f, and e≤2f, so as to prevent the binding wire 22 from being hooked on the valley. In the present embodiment, the limiting ring buckles 24 are disposed on the waveform ring 1011 to not only facilitate radial compression of the stent, but to also reduce the risk of damage to the covering film by the binding wire 22.

Figure 21:
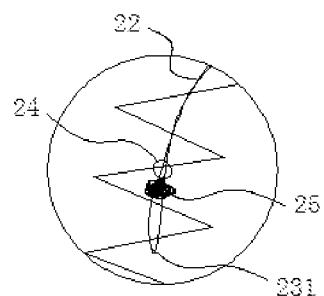
FIG. 21 is a schematic diagram of a positioning member disposed on the binding wire of the lumen stent of FIG. 14.
Figure 22:
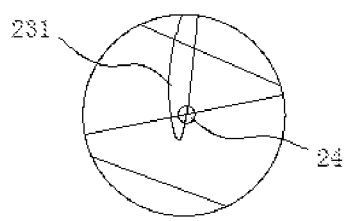
FIG. 22 is a schematic diagram of the first lock catch of the lumen stent of FIG. 14 coupled together with the limiting ring buckle.

An anti-disengagement structure is disposed between the lock catch assembly 23 and the limiting ring buckle 24, so that the lock catch assembly 23 is prevented from sliding down from the limiting ring buckle 24 after the restraint is relieved, and the binding wire 22 is axially displaced. In the embodiment shown in FIG. 21, the anti-disengagement structure is a positioning member disposed at the junction of the binding wire 22 and the first lock catch 231. The positioning member 25 has an outer diameter greater than an inner diameter of the limiting ring buckle 24 so that the positioning member 25 cannot pass through the limiting ring buckle 24. It is to be understood that the present embodiment does not limit the specific position of the positioning member 25 on the binding wire 22. For example, in other embodiments, the positioning member 25 is located between the two limiting ring buckles 24. It is also to be understood that, in other embodiments, an anti-disengagement structure may not be provided and that the lock catch assembly 23 and the limiting ring buckle 24 may be prevented from being disengaged in other manners. For example, in the embodiment shown in FIG. 22, the first lock catch 231 is hooked with the limiting ring buckle 24 to prevent the lock catch assembly 23 from sliding down from the limiting ring buckle 24.

It is to be understood that if the size of the limiting ring buckle 24 is too large, the range of movement of the binding wire 22 in the axial direction is large, and the radial compression effect of the stent is affected. But if the size of the limiting ring buckle 24 is too small, the friction force between the limiting ring buckle 24 and the binding wire 22 is increased, and the circumferential relative movement thereof is also affected, which is unfavorable for the stent to be smoothly expanded. Therefore, in the present embodiment, the ratio of the area of the limiting ring buckle 24 to the cross-section area of the binding wire 22 is between 1.1-2. It is to be noted that when the limiting ring buckle 24 is annular, the "area of the limiting ring buckle 24" refers to the in-ring area of the limiting ring buckle. When the limiting ring buckle 24 is a line segment having both ends fixed on the tubular body 11, the "area of the limiting ring buckle 24" refers to the area enclosed by the limiting ring buckle 24 and the tubular body 11.

Figure 23:
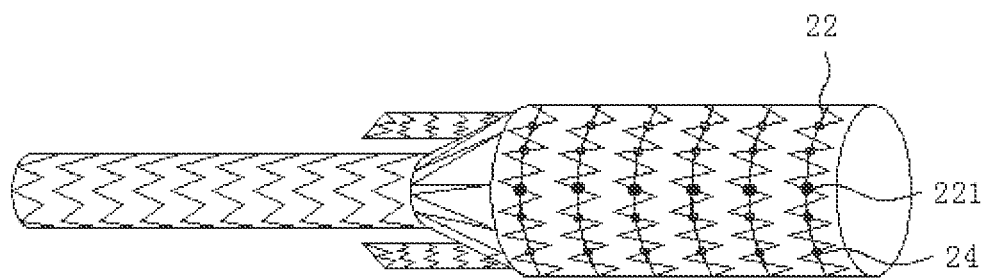
FIG. 23 is a rear view of the lumen stent of FIG. 15.

Referring to FIG. 23, the binding wire 22 further includes at least one fixing portion 221. The fixing portion 221 may be fixed on the tubular body 11 by suture or adhesion or the like. When the binding wire 22 slides down from all the limiting ring buckles 24, the fixing portion 221 may prevent the binding wire 22 from entering the downstream vessel after being disengaged from the stent.

In the present embodiment, the binding wire 22 may be a flexible wire having a high tensile strength, such as a polyester suture. The binding wire 22 may consist of a single flexible wire or may consist of multiple flexible wires. The limiting ring buckle 24, the first lock catch 231 and the second lock catch 232 may be polyester suture coils or nitinol rings and the like. The limiting rod 21 may be a metal wire having a small surface roughness and good biocompatibility with the human body, such as a nitinol wire. In order not to increase the overall outline size of the stent and in order to avoid stress bending of the limiting rod 21, the wire diameter of the limiting rod 21 is between 0.2-0.6 mm. Further, in order to reduce resistance when the limiting rod 21 is withdrawn, the ratio of the area of the first lock catch 231 or the second lock catch 232 to the cross-section area of the limiting rod 21 is between 1.5-3. It is to be noted that when the first lock catch 231 or the second lock catch 232 is annular, the "area of the first lock catch 231 or the second lock catch 232" refers to the in-ring area of the first lock catch 231 or the second lock catch 232. When the first lock catch 231 or the second lock catch 232 is a line segment having both ends fixed on the tubular body 11, the "area of the first lock catch 231 or the second lock catch 232" refers to the area enclosed by the first lock catch 231 or the second lock catch 232 and the tubular body 11.

In the embodiment shown in FIG. 14 and FIG. 15, the binding wire 22 restrains the entire circumference of the lumen stent 100 when the limiting rod 21 is inserted through the lock catch assembly 23. It is to be understood that in other embodiments, the binding wire 22 may circumferentially restrain only a portion of the region of the lumen stent 100 when the limiting rod 21 is inserted through the lock catch assembly 23. However, if the range of a restraint region where the binding wire 22 carries out circumferential restraint is too small, a stent in the restraint region may be more compressed in a radial direction. In the expansion process of the stent, the defect that the stent in the restraint region is not fully expanded and stents in other regions are attached to the wall may occur, so that larger grooves exist in the restraint region, the stent is not well attached to the wall as a whole, and the risk of internal leakage is increased. Therefore, in the present embodiment, when the limiting rod 21 is inserted through the lock catch assembly 23, an angle in the circumferential direction of the restraint region where the binding wire 22 circumferentially restrains the tubular body 11 is about 180°-360°.

Figure 24:
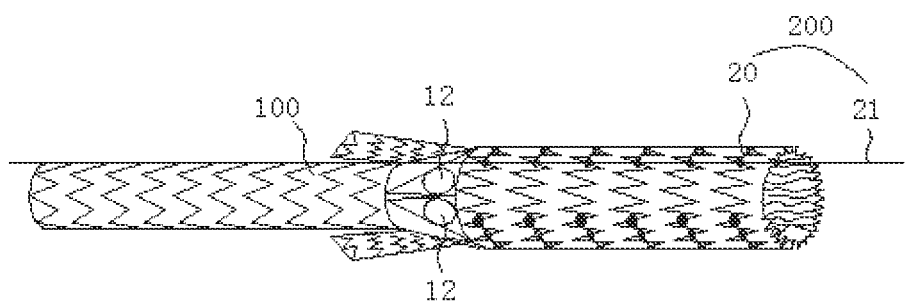
FIG. 24 is a schematic diagram of a lumen stent according to a third exemplary embodiment of the application in a partial-release state.
Figure 25:
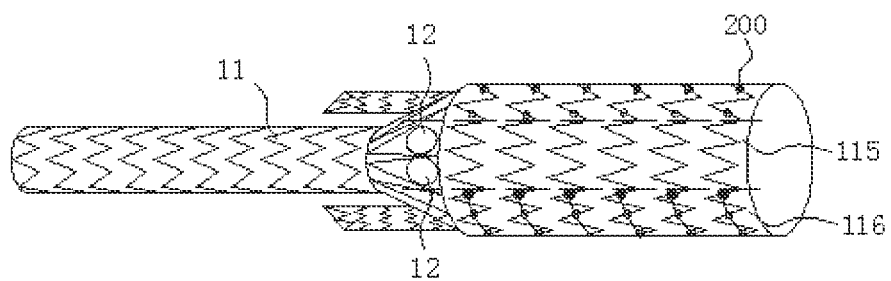
FIG. 25 is a schematic diagram of the lumen stent of FIG. 24 when fully expanded.

Referring to FIG. 24 and FIG. 25, a third exemplary embodiment of the present application provides an implant which is a lumen stent 100 that is substantially the same as the lumen stent of the second embodiment. The lumen stent 100 includes a tubular body 11 and a partial-release device 200 connected to an outer surface of the tubular body 11. The third embodiment differs from the second embodiment in that the tubular body 11 includes, in a circumferential direction, a first region 115 and a second region 116. Two inner branches 12 on the tubular body 11 are located within the first region 115, and the partial-release device 200 is disposed within the second region 116.

The partial-release device 200 of the present embodiment avoids a region where the inner branch 12 of the lumen stent 100 is located and locally restrains a region outside the inner branch 12. When the lumen stent 100 is in a partial-release state, the region where the inner branch 12 of the lumen stent 100 is located is fully expanded, and at this moment, the inner branch 12 can be accurately positioned. Moreover, when the restraint of the partial-release device 200 is relieved, the restraint part of the lumen stent 100 is gradually expanded, and the region where the inner branch 12 is located has no expansion motion, so that a circumferential alignment error of the inner branch 12 is greatly reduced.

It is to be understood that, if the range of a circumferential restraint region of the second region 116 is too small, a stent in the restraint region may be more compressed in a radial direction. In the expansion process of the stent, the defect that the stent in the restraint region is not fully expanded and stents in other regions are attached to the wall may occur, so that larger grooves exist in the restraint region, the stent is not well attached to the wall as a whole, and the risk of internal leakage is increased. However, if the range of the circumferential restraint region of the second region 116 is too large, the installation of the inner branch 12 may be affected. Therefore, referring to FIG. 25, when the lumen stent 100 is fully expanded, the second region 116 covers a circumferential angle of about 180°-340°.

The ratio of a cross-section circumscribed circle diameter of the first body segment 111 in a partial-release state to a cross-section circumscribed circle diameter of the unexpanded first body segment 111 is also between 0.6-0.8 in order to reduce the circumferential and axial positioning deviations, and to avoid the wall attachment of the stent during positioning adjustment.

Since the specific structure of the partial-release device 200 of the third embodiment is the same as that of the second embodiment, the specific structure of the partial-release device 200 will not be described in detail.

Figure 26:
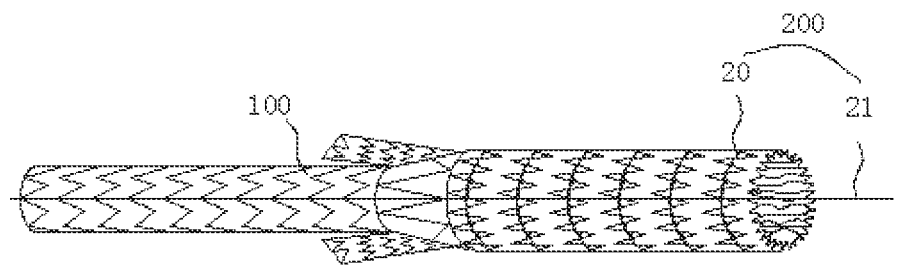
FIG. 26 is a schematic diagram of a lumen stent according to a fourth exemplary embodiment of the application in a partial-release state.
Figure 27:
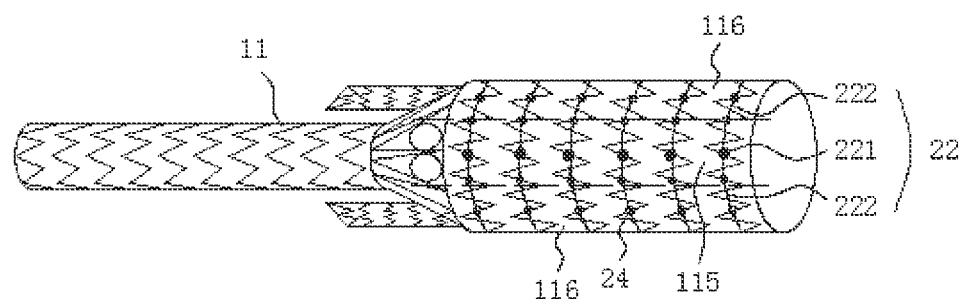
FIG. 27 is a schematic diagram of the lumen stent of FIG. 26 when fully expanded.
Figure 28:
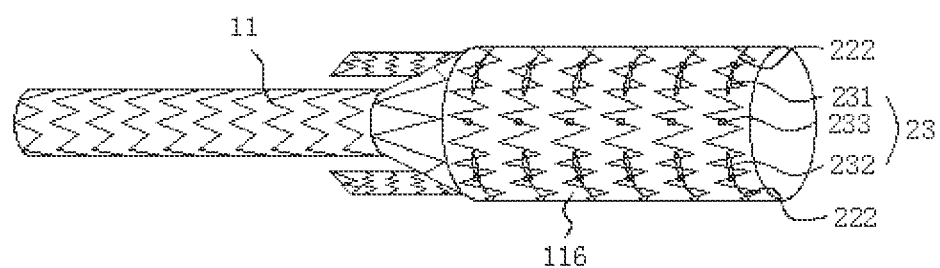
FIG. 28 is a rear view of the lumen stent of FIG. 26.

Referring to FIG. 26, FIG. 27 and FIG. 28, a fourth exemplary embodiment of the present application provides an implant which is a lumen stent 100 that is substantially the same as the lumen stent of the second embodiment. The lumen stent 100 includes a tubular body 11 and a partial-release device 200 connected to an outer surface of the tubular body 11. The partial-release device 200 includes a limiting rod 21, and a plurality of binding units 20 movably connected to the limiting rod 21. The limiting rod 21 is movably inserted through the binding units 20.

The fourth embodiment differs from the second embodiment in that the tubular body 11 includes, in a circumferential direction, a first region 115 and a second region 116. Two inner branches 12 are located within the first region 115. The binding unit 20 includes a binding wire 22 and a lock catch assembly 23. The binding wire 22 includes a fixing portion 221 fixedly connected within the first region 115, and two binding portions 222 respectively extending from both sides of the fixing portion 221. The lock catch assembly 23 is respectively connected to the two binding portions 222 and is located within the second region 116. When the limiting rod 21 is inserted through the lock catch assembly 23, the binding wire 22 circumferentially restrains the tubular body 11 nearby.

Since the two binding portions 222 of the binding wire 22 respectively extend from both sides of the fixing portion 221 into the second region 115, when the restraint of the limiting rod 21 is relieved, the two binding portions 222 respectively move circumferentially in opposite directions; i.e., the forces acting on the tubular body 11 by the two binding portions 222 respectively may be at least partially offset, thereby ensuring the tubular body 11 to be smoothly expanded in the process of relieving the restraint. Moreover, since the fixing portion 221 of the binding wire 22 and the inner branch 12 are both located within the first region 115, the fixing portion 221 does not move circumferentially in the process of relieving the restraint, so that the first region 115 where the fixing portion is located is more stable during expansion, and the circumferential alignment error of the inner branch 12 is greatly reduced. In the present embodiment, the lengths of the two binding wires 22 are equal, so that the forces acting on the tubular body 11 by the two binding portions 222 respectively are all offset.

Referring to FIG. 28, the plurality of binding units 20 are uniformly distributed on the outer surface of the tubular body 11, and each binding unit 20 is distributed in a circumferential direction. The lock catch assembly 23 includes a first lock catch 231, a second lock catch 232 and a third lock catch 233. The first lock catch 231 and the second lock catch 232 are respectively connected to the two binding portions 222, and the third lock catch 233 is connected to the tubular body 11. When the limiting rod 21 is inserted through the first lock catch 231 and the second lock catch 232, the binding wire 22 circumferentially restrains the tubular body 11 nearby, and after being accurately positioned, the limiting rod 21 is pulled out from the first lock catch 231 and the two second lock catches 232 so as to relieve the restraint. It is to be understood that in other embodiments, the lock catch assembly 23 includes only the first lock catch 231 and the second lock catch 232, or the first lock catch 231 and the third lock catch 233.

Further, the binding unit 20 also includes at least one limiting ring buckle 24. The limiting ring buckle 24 is fixed on the tubular body 11. The binding wire 22 and/or the lock catch assembly 23 penetrate from one side of the limiting ring buckle 24 to the other side.

In the present application, the plurality of limiting ring buckles 24 are disposed on the outer surface of the tubular body 11, and the binding wire 22 and/or the lock catch assembly 23 penetrate through the limiting ring buckles 24. Moreover, when the lumen stent 100 is compressed within the delivery sheath or the restraint of the binding wire 22 on the lumen stent 100 is relieved, the limiting ring buckle 24 also prevents axial displacement of the binding wire 22.

Like the second embodiment, the present embodiment does not limit the specific structure of the first lock catch 231 and the second lock catch 232, and the first lock catch 231 and the second lock catch 232 may have an annular structure, or may have other structures as long as the limiting rod 21 is movably connected within the first lock catch 231 and the second lock catch 232. For example, in the embodiment shown in FIG. 17, the first lock catch 231 is hooked on the limiting ring buckle 24; i.e., the first lock catch 231 is folded in reverse after penetrating from one side to the other side of the limiting ring buckle 24. At this moment, the binding wire 22 and the first lock catch 231 are of an integrated structure.

Since the structure, number and fixing position of the limiting ring buckle 24, the relationship among the limiting ring buckle 24, the binding wire 22 and the lock catch assembly 23, and the relationship between the limiting rod 21 and the lock catch assembly 23, are the same as those of the first embodiment, they will not be described in detail.

In the embodiment shown in FIG. 26, FIG. 27 and FIG. 28, the binding wire 22 restrains the entire circumference of the lumen stent 100 when the limiting rod 21 is inserted inside the lock catch assembly 23. It is to be understood that in other embodiments, the binding wire 22 may circumferentially restrain only a portion of the region of the lumen stent 100 when the limiting rod 21 is retained inside the lock catch assembly 23. However, if the range of a circumferential restraint region of the binding wire 22 is too small, a stent in the restraint region may be more compressed in a radial direction. In the expansion process of the stent, the defect that the stent in the restraint region is not fully expanded and stents in other regions are attached to the wall may occur, so that larger grooves exist in the restraint region, the stent is not well attached to the wall as a whole, and the risk of internal leakage is increased. Therefore, in the present embodiment, when the limiting rod 21 is inserted through the lock catch assembly 23, an angle in the circumferential direction of the restraint region where the binding wire 22 circumferentially restrains the tubular body 11 is about 180°-360°.

The various technical features of the above-described embodiments may be combined in any combination, and in order to simplify the description, all possible combinations of the various technical features in the above-described embodiments are not described. However, as long as the combinations of these technical features do not contradict, they should be considered to be the scope of the description.

The above-described examples express only a few implementations of the application, which are described in greater detail but are not to be construed as limiting the scope of the application. It will be appreciated by those of ordinary skill in the art that numerous variations and modifications may be made to the application without departing from the concept of the application, which fall within the protection scope of the application. Therefore, the protection scope of the application should be determined by the appended claims.

The invention claimed is:

1. A lumen stent, comprising a tubular body, an inner branch and an outer branch which are respectively communicated with the tubular body, the tubular body comprising a first body segment, a tapered segment and a second body segment which are connected in sequence, wherein the tapered segment is provided with an outer branch window and an inner branch window, with all the outer branch windows and all the inner branch windows located only on the tapered segment, a proximal end of the outer branch being connected to the outer branch window prior to implantation, a distal end of the inner branch being connected to the inner branch window, and the area of the inner branch window being larger than that of the outer branch window, wherein the inner branch is a first inner branch, and further including a second inner branch, and waveform rings on the first and second inner branches are distributed in a staggered manner.

2. The lumen stent according to claim 1, characterized in that the tapered segment is provided with a waveform ring comprising a plurality of peaks, a plurality of valleys and a plurality of connecting rods respectively connecting adjacent peaks and valleys, the outer branch window being located distal to the plurality of peaks, and/or the inner branch window being located proximal to the plurality of valleys.

3. The lumen stent according to claim 2, characterized in that at least one of the plurality of peaks and at least one of the plurality of valleys is disposed between the inner branch window and the outer branch window.

4. The lumen stent according to claim 2, characterized in that the inner branch window is a first inner branch window, and further including a second inner branch window located on the tapered segment, with a peak being disposed between the first and second inner branch windows, and a waveform angle of the peak being between 0-10°.

5. The lumen stent according to claim 1, characterized in that the distal end of the inner branch is located proximal to a distal end of the outer branch.

6. The lumen stent according to claim 1, characterized in that the distal end of the first inner branch has an outer wall, the second inner branch having a distal end that has an outer wall, and wherein the outer wall of the distal end of the first inner branch and the outer wall of the distal end of the second inner branch are in closed connection with an inner wall of the tubular body.

7. The lumen stent according to claim 1, characterized in that a proximal end surface of the first inner branch is inclined with respect to a longitudinal center axis of the inner branch, and/or a distal end surface of the outer branch is inclined with respect to a longitudinal center axis of the outer branch.

8. The lumen stent according to claim 7, characterized in that an angle between the proximal end surface of the inner branch and the longitudinal center axis of the first inner branch is between 30°-60°, and/or an angle between the distal end surface of the outer branch and the longitudinal center axis of the outer branch is between 30°-60°.

9. The lumen stent according to claim 1, characterized in that an outer surface of the tubular body is provided with a partial-release device.

10. The lumen stent according to claim 1, characterized in that the first inner branch has a proximal end, the first body segment has a proximal end, and an outer wall of the first body segment is provided with a barbed structure located between the proximal end of the inner branch and the proximal end of the first body segment.

11. The lumen stent according to claim 1, characterized in that the first inner branch has a proximal end, the first body segment has a proximal end, and a vertical distance between the proximal end of the inner branch and the proximal end of the first body segment is not less than 20 mm.

12. The lumen stent according to claim 1, characterized in that the outer branch is permanently fixed to the outer branch window prior to implantation.

13. The lumen stent according to claim 1, characterized in that the first inner branch has a distal end, and the first inner branch and the second inner branch are respectively communicated with the tubular body, the outer branch is a first outer branch, and further including a second outer branch which has a proximal end, and the first outer branch and the second outer branch are respectively communicated with the tubular body, and an imaging mark for positioning the first inner branch, the second inner branch, the first outer branch and the second inner branch wherein the distal end of the first inner branch is connected to the tapered segment, the proximal end of the first outer branch is connected to the tapered segment, the first inner branch and the second inner branch are located between the first outer branch and the second outer branch, an angle between the first inner branch and the first outer branch in a circumferential direction is 60-80°, and an angle between the first outer branch and the second outer branch in the circumferential direction is 170-180°.

14. The lumen stent according to claim 1, characterized in that each of the inner branches and the outer branch are communicated with the tubular body respectively, wherein the distal end of the first inner branch is connected to the tapered segment, a proximal end of the outer branch is connected to the tapered segment, and a distal waveform ring of the inner branch is located distal to a proximal waveform ring of the outer branch.

15. The lumen stent according to claim 1, characterized in that each of the inner branches and the outer branch are respectively communicated with the tubular body, wherein the distal end of the first inner branch is connected to the tapered segment, a proximal end of the outer branch is connected to the tapered segment, and the distal end of the inner branch is located distal to the proximal end of the outer branch.

16. The lumen stent according to claim 1, characterized in that a partial-release device is connected to an outer surface of the tubular body, wherein the partial-release device comprises a limiting rod and a binding unit movably connected to the limiting rod, the binding unit comprising a binding wire, a lock catch assembly and at least one limiting ring buckle, the lock catch assembly being connected to the binding wire, the limiting ring buckle being fixed on the tubular body, the binding wire and/or the lock catch assembly penetrating from one side of the limiting ring buckle to the other side, and when the limiting rod penetrates into the lock catch assembly, the binding wire restrains the tubular body circumferentially.

17. The lumen stent according to claim 16, characterized in that the lock catch assembly comprises a first lock catch connected to the binding wire and a second lock catch connected to the binding wire or/and the tubular body, the limiting rod being movably connected within the first lock catch and the second lock catch.

18. The lumen stent according to claim 1, characterized in that a partial-release device is connected to an outer surface of the tubular body, wherein the partial-release device comprises a limiting rod and a binding unit movably connected to the limiting rod, the tubular body comprises a first region and a second region in a circumferential direction, the binding unit is disposed in the second region, the binding unit comprises a binding wire and a lock catch assembly connected to the binding wire, and when the limiting rod penetrates into the lock catch assembly, the binding wire restrains the tubular body circumferentially, and wherein a fixing portion of the binding wire and the first inner branch are both located within the first region.

19. The lumen stent according to claim 1, characterized in that a partial-release device is connected to an outer surface of the tubular body, wherein the partial-release device comprises a limiting rod and a plurality of binding units movably connected to the limiting rod, the binding unit comprising a binding wire and a lock catch assembly, the binding wire comprising a fixing portion fixedly connected to the tubular body, and two binding portions respectively extending from both sides of the fixing portion, the lock catch assembly being respectively connected to the two binding portions, and when the limiting rod penetrates into the lock catch assembly, the binding wire restrains the tubular body circumferentially.

20. The lumen stent according to claim 1, characterized in that the inner branch window is a first inner branch window, and further including a second inner branch window, and the first inner branch window and the second inner branch window are located at the same level.

\* \* \* \* \*